US011110398B2

(12) United States Patent
Nutalapati et al.

(10) Patent No.: US 11,110,398 B2
(45) Date of Patent: Sep. 7, 2021

(54) METHOD FOR ENHANCING FILTRATION YIELDS IN TANGENTIAL FLOW FILTRATION SYSTEM

(71) Applicant: Cytiva Sweden AB, Uppsala (SE)

(72) Inventors: Sasi Kumar Nutalapati, Bangalore (IN); Klaus Gebauer, Uppsala (SE); Karl Axel Jakob Liderfelt, Uppsala (SE); Nachiket Karmarkar, Bangalore (IN); Ajit S. Vernekar, Bangalore (IN); Amit Kumar Sharma, Bangalore (IN); Fredrik Oskar Lundstrom, Uppsala (SE); Sangeetha Raghu Ramachandran, Bangalore (IN)

(73) Assignee: Cytiva Sweden AB, Uppsala (SE)

( * ) Notice: Subject to any disclaimer, the term of this patent is extended or adjusted under 35 U.S.C. 154(b) by 0 days.

(21) Appl. No.: 15/750,218

(22) PCT Filed: Aug. 17, 2016

(86) PCT No.: PCT/EP2016/069475
§ 371 (c)(1),
(2) Date: Feb. 5, 2018

(87) PCT Pub. No.: WO2017/029307
PCT Pub. Date: Feb. 23, 2017

(65) Prior Publication Data
US 2018/0221822 A1  Aug. 9, 2018

(30) Foreign Application Priority Data

Aug. 20, 2015 (IN) ............................ 2581/DEL/2015
Aug. 21, 2015 (IN) ............................ 2610/DEL/2015

(51) Int. Cl.
*C07K 1/34* (2006.01)
*B01D 61/18* (2006.01)
(Continued)

(52) U.S. Cl.
CPC ............. *B01D 61/18* (2013.01); *B01D 61/08* (2013.01); *B01D 61/10* (2013.01); *B01D 61/12* (2013.01);
(Continued)

(58) Field of Classification Search
CPC ........ B01D 61/08; B01D 61/10; B01D 61/12; B01D 61/14; B01D 61/145; B01D 61/18;
(Continued)

(56) References Cited

U.S. PATENT DOCUMENTS 6,106,727 A * 8/2000 Krasnoff ............. A61M 1/0227
210/739
8,845,902 B2 9/2014 Pralong et al.
(Continued)

FOREIGN PATENT DOCUMENTS

EP      2708249 B1    7/2016
JP      H09-40092 A   2/1997
WO      2011/161609 A1 12/2011

OTHER PUBLICATIONS

PCT International Search Report and Written Opinion for PCT Application No. PCT/EP2016/069475 dated Oct. 25, 2016 (10 pages).
(Continued)

*Primary Examiner* — Hayden Brewster
(74) *Attorney, Agent, or Firm* — Eversheds Sutherland (US) LLP

(57) ABSTRACT

The disclosure generally relates to methods and apparatus for the efficient quantitative recovery of valuable biological fluids from filtration systems, more particularly to efficient quantitative recovery of valuable biological fluids from high precision separation systems suitable for use in the pharmaceutical and biotechnology industries.

12 Claims, 1 Drawing Sheet

(51) Int. Cl.
  *B01D 61/20* (2006.01)
  *B01D 61/22* (2006.01)
  *B01D 61/08* (2006.01)
  *B01D 61/10* (2006.01)
  *B01D 61/12* (2006.01)
  *B01D 65/02* (2006.01)

(52) U.S. Cl.
  CPC ............. *B01D 61/20* (2013.01); *B01D 61/22* (2013.01); *B01D 65/02* (2013.01); *C07K 1/34* (2013.01); *B01D 2311/08* (2013.01); *B01D 2311/16* (2013.01); *B01D 2311/25* (2013.01); *B01D 2313/243* (2013.01); *B01D 2315/10* (2013.01); *B01D 2315/14* (2013.01); *B01D 2321/02* (2013.01)

(58) Field of Classification Search
  CPC ........ B01D 61/20; B01D 61/22; B01D 61/24; B01D 61/243; B01D 61/246; B01D 61/28; B01D 63/02; B01D 65/02; B01D 2311/08; B01D 2311/16; B01D 2311/25; B01D 2313/243; B01D 2315/10; B01D 2315/14; B01D 2321/02; C07K 1/34; C07K 16/00; C12M 1/00; C12M 3/06; C12M 47/10; C12N 5/071

USPC ........................................... 210/636; 137/561
See application file for complete search history.

(56) References Cited

U.S. PATENT DOCUMENTS

| | | |
|---|---|---|
| 2003/0116487 A1 | 6/2003 | Petersen |
| 2005/0023194 A1 | 2/2005 | Petersen et al. |
| 2006/0027500 A1 | 2/2006 | Schick et al. |
| 2007/0215474 A1* | 9/2007 | Batchelder ........... B01D 61/422 204/524 |
| 2013/0029411 A1 | 1/2013 | Roy et al. |
| 2013/0240065 A1* | 9/2013 | Weissenbach ......... B01D 61/20 137/561 R |
| 2015/0079194 A1* | 3/2015 | Hanna .................... B01D 69/02 424/530 |
| 2017/0056825 A1 | 3/2017 | Schwan et al. |

OTHER PUBLICATIONS

Japanese Office Action for JP Application No. 2018-507721 dated Jun. 1, 2020 (12 pages with English translation).
Chinese Office Action for CN Application No. 201680047998.8 dated May 27, 2020 (15 pages with English translation).

* cited by examiner

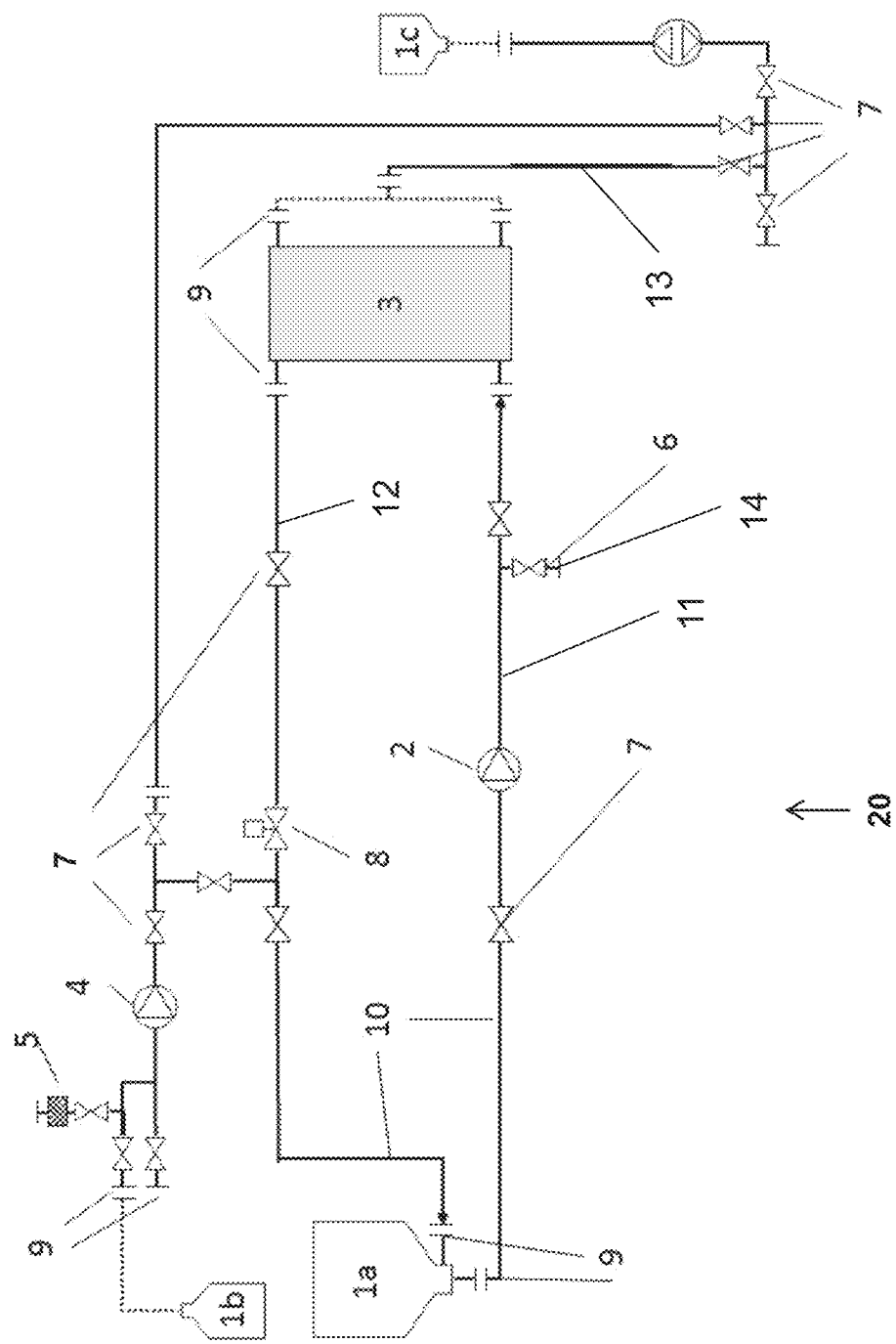

METHOD FOR ENHANCING FILTRATION YIELDS IN TANGENTIAL FLOW FILTRATION SYSTEM

CROSS REFERENCE TO RELATED APPLICATIONS

This application claims the priority benefit of PCT/EP2016/069475 filed on Aug. 17, 2016 which claims priority benefit of India Application Nos. 2581/DEL/2015 and 2610/DEL/2015 filed Aug. 20 and Aug. 21, 2015, respectively. The entire contents of which are hereby incorporated by reference herein.

FIELD

The disclosure generally relates to methods and apparatus for the efficient quantitative recovery of valuable biological fluids from filtration systems, more particularly to efficient quantitative recovery of valuable biological fluids from high precision separation systems suitable for use in the pharmaceutical and biotechnology industries.

BACKGROUND

Filtration systems are a critical component of the pharmaceutical and biotechnology industries for purifying biofluids. Due to the high value of the purified biofluid extensive research has been focused on improving all aspects of the filtration systems. Such filtration systems also cover a broad spectrum of utility including micro-filtration, ultrafiltration, tangential or cross-flow filtration, as well as constant volume diafiltration. Generally, in these systems, the liquid to be filtered is forced through a flowpath to a porous membrane sheet or a porous hollow fiber column. Such sheets or membranes are commercially available and utilizing these different pore sizes molecules or particulates smaller than the average membrane or column pore size will pass, together with solvent for example, through the membrane or hollow fiber walls and are collected as filtrate. A retentate flow is left behind. In many filtration approaches, such as those incorporating ultrafiltration or other tangential-flow filtration devices, the retentate is repeatedly re-circulated with the objective of improving filtration efficiency and enhancing the yield of the filtrate or permeate. Each of these flow contains valuable product up to 1-5% of the total recovery potential. Examples of such systems can be found in U.S. Pat. No. 6,607,669 to Schick issued Aug. 19, 2003; U.S. Pat. No. 7,270,744 to Petersen issued Sep. 18, 2007; U.S. Pat. No. 6,461,513 and International Patent Publication WO 2014/051503 published Apr. 3, 2014.

Quantitative recovery of the valuable concentrated biofluids after purification and or concentration is one area of interest. Once maximal purification and/or concentration processing is complete a significant amount of residual biofluid remains in the flowpath of the filtration system. Numerous strategies have been applied to facilitate recovery of this residual biofluid. Unfortunately none of these methods has resulted in the efficient and quantitative recovery of all residual biofluid.

Filtration technology is also encumbered with many known disadvantages such as the very labor intensive nature of the activity. Additional, serious shortcomings affect safety and efficiency. One shortcoming is that the filtrate yield is frequently not quantitative because of unpredictable solution particulate loads. Another shortcoming is excessive filter inlet pressure which leads to blow-off of tube connections such as at the filter inlet, resulting in costly spillage of retentate, for example. Further, the present methods facilitate the reduction of cost for equipment and operation because the recovery system requires just an additional inlet with a sterile filter, while traditional air blow down requires more equipment, an external pressure source, and manual interaction. Because of these types of shortcomings, manual and semi-automated filtration systems need to be constantly monitored, which greatly contributes to the high labor intensity of such approaches.

Current biofluid recovery practice involves the application of a pressurized air line at the biofluid reservoir inlet to blow down the product from flow path. Such method unfortunately often leads to foaming of the residual fluid, degradation of the quality of the biofluid and loss of sterile conditions. Improved methods to recover the biofluid retained in the crossflow filtration system are needed.

In this disclosure, an internal Flow Pump is used to pressurize and force the concentrated product out of the Crossflow Filtration system for maximum recovery of the residual biofluid.

SUMMARY

As described herein, the exemplary embodiments overcome one or more of the above or other disadvantages known in the art. Briefly, the present disclosure provides for the efficient quantitative recovery of valuable biological fluids from filtration systems, more particularly to efficient quantitative recovery of valuable biological fluids from high precision separation systems suitable for use in the pharmaceutical and biotechnology industries. More specifically the disclosure relates to methods, processes, systems and apparatus for recovering residual (concentrated) biofluid product from a Crossflow Filtration system after desired separation has been completed such as with concentration or diafiltration applications. After these processes have completed, the concentrated biofluid remaining in the Crossflow Filtration Flowpath can be recovered by the internal application of pressure and sterile air to the Crossflow Filtration system such that the residual fluids in the crossflow filtration system are efficiently recovered at a collection drain point (which may be located at the lowest point of the system).

More specifically, the disclosure relates to a method/process/system for enhanced recovery of an valuable Biological Fluid from an activated Crossflow Filtration System comprising: inducing an internalized (integrated) pressurized Countercurrent Flow throughout the Crossflow Filtration System by activating a Internal Pump (such as a Peristaltic pump) operably linked to a Sterile Air Source at one end of the Crossflow Filtration System, and recovering said valuable Biological Fluid at a Drain Valve operably linked at the opposite end of the Crossflow Filtration System.

The Crossflow Filtration System comprises:
i. a Biofluid Container,
ii. a Crossflow Filtration Filter,
iii. a Feed Flow Line operably linked from said Biofluid Container to said Crossflow Filtration Filter containing Feed Flow,
iv. a Retentate Flow Line Return operably linked from said Crossflow Filtration Filter to said Biofluid Container; said Retentate Flow Line Return containing unFiltered Flow,
v. a Permeate Flow Line operably linked to said Crossflow Filtration Filter containing (filtered) Permeate Flow;
vi. an Internal Pump operably linked to said Retentate Flow Line Return and a Sterile Air Source, vii. A Drain Line operably linked (Valve) to said Feed Flow Line;

viii. wherein said Internal Pump is activated pressurizing Counter-Current Flow throughout said Crossflow filtration System from the operably linked Pump/Sterile Air Source to said Drain Valve wherein said valuable flow is recovered.

This recovered product is a concentrated biofluid and is highly valued and thus should be maximally recovered from the system flow path for further processing. This process enables a user to completely drain out product from the Crossflow system particularly the Flowpath without any dilution. Although not to be limited to any particular theory, one aspect of the present disclosure relates to the specific use of internal pressure to the Cross-Flow Filtration System so as to effectively shear the residual concentrated biofluid from the system flow surfaces surprisingly without any degradation of the product and enhancing the overall yield at the Drain. Use of an internal pump/pressure also facilitates accurate and targeted control of pressure and integration to electronic data processing network.

Traditionally, recovery focuses on a so-called holdup volume which refers to the residual fluid remaining in the system after completion of filtration. Methods for recovering the holdup volume include Gravity based recovery, which as it states relies on gravitational forces to drain residue from a Crossflow system. Such methods can be perfected to yield about 33% of the holdup volume. Adding pressure from a Feed Pump may allow for a recovery of an additional 44% of holdup volume. Recovering the remaining 23% has been an ongoing challenge and although externally applied air pressure has been used is some applications for collection the associated risk factors of such method including inability to control pressure have not yielded quantitative recovery. Another standard method to recover the product is by buffer flush of the Crossflow Filtration system after the final biofluid concentration. Unfortunately, this method results in dilution of the final valued product. Another standard method to recover the complete product is to pump out the product by running the feed pump. Unfortunately, this method also fails to recover the complete product.

So-called Air Blow Down is yet another method that has been used to recover product from the Flowpath. This method requires opening the Cross-flow filtration system and connecting an industrial air line that delivers a pressurized volume of air to blow down the biofluid from the Flowpath. Such method can result in the creation of foaming in the biofluid requiring additional processing steps before recovery of the biofluid. Furthermore, the loss of system and sterile control coupled with discontinuity to the integrity of the closed continuously cycling system may be detrimental to the value of the biofluid fraction.

Using the current methods an additional 11-20% can be recovered although importantly the entire 88-98% can be recovered in one step in a fraction of the time and risk of standard methods. The present process is thus a significant improvement over the results from existing technologies.

The present disclosure is applicable to a variety of separation techniques such as microfiltration, microparticle coating and washing, ultrafiltration, diafiltration and certain preparative chromatography applications. It is also applicable to automated viral infection of mammalian cells such as in gene therapy research and development, as well as rapid cell separation, protein clarification and protein concentration. Each of these systems may be easily redesigned in a yield-enhancing manner according to the present disclosure and can be automated.

One embodiment of the present disclosure relates to recovery from an activated Crossflow Filtration system. Activated as used herein refers to a crossflow filtration system that has been constructed, loaded and standard filtration and/or fluid concentration has been completed. Thus, a filtration system is deemed activated once the system is loaded with the biofluid of interest and homeostatic continuous cyclic flow has been established. At this concluding period in a crossflow filtration system the user would like to quickly and efficiently recover all of the residual biofluid remaining in the system Flowpath. Activation includes methods to isolate and stabilize the system after filtration is complete. Frequently the valves to and from the biofluid reservoir are closed. However, the present processes offer a continuous and seamless transition from standard concentration or collection to a pressurized draining of the residual fluids from the flowpath. Maintaining the sterility and integrity of the Cross Flow System without any external action required by a user greatly enhances the yield of the overall process. The methods of the present disclosure involve the recovery of the biofluid from this activated system.

Biofluids as used herein refers to fluids prepared by biological or pharmaceutical methods and contain biological agents such as cells, molecules (particularly valuable proteins), suspended particles, media, buffer, carrier, reaction solution, or other liquid component. The scope of fluids used in Crossflow filtration systems is well known.

Pumps as used herein refers to positive displacement pumps including peristaltic pumps for the permeate and transfer and diaphragm pumps for Feed. Additionally, there are centrifugal pumps available for filtration application. Properties of the pump include low shear pressure/flow specification and a disposable pump head which can be part of single use flowpath.

The Internal Pump refers to a positive displacement pump that is integrated into the Flowpath. Internal pumps ideally have a low shear pressure/flow specification and a disposable pump head which integrally enables the single use aspect of the Flowpath.

Another embodiment relates to recovery by automation of the pressurization method such that the pump and air source including associated valves is provided and linked with an electronic data processing network for receiving, processing, and recording data associated with the operation of, for example, the device's pumps, valves, and sensors, as well as from an external source (i.e., user input), and for transmitting signals (or other electronic instructions) to, for example, said pumps, valves, and sensors. The data processing network will comprise circuitry, wiring, a user interface, data storage media, at least one CPU, and other electronic components, arranged to effect electronic connectivity and control of the device's components.

Another embodiment relates to multiple bay inlet/outlet Crossflow systems. Although standard operation envisions biofluid contained in the biofluid container, in typical practice, the container is not the starting point or origin of said biofluid. Rather, the typical source of fluid dispensed into system is a multi-vessel liquid sample dispenser. An example of such multibay insertion is schematically illustrated in FIG. 1. As shown therein, a multi-vessel sample dispenser may be integrated into the system through connection 9 which is ultimately linked to the biofluid container 1a. Multi-vessel sample dispenser such as 1b may comprise multiple solution vessels each controlled by an electronically-controllable valve, and capable of being filled or otherwise loaded with varying solutions of fluid according to the process parameters of the particular separation application being pursued. Thus, for example, these vessels can be filled with alternating solutions of deionized water, cleaning solution, buffer solution, and biochemical sample solution. The solutions are dispensed independently or in mixture under the electronic control of the system's data processing network according to a preprogrammed regimen.

Another embodiment relates to a single use system.

The tangential or Crossflow filtration filter is a filtration device in which a large fraction of the biofluid flows continuously, over time, in a direction essentially parallel to a membrane surface (containing pores of various sizes), as opposed to a much smaller portion which flows through the membrane. Because of the sweeping, cleansing nature of such flow—which discourages premature clogging, fouling, and concentration polarization—crossflow (also known as tangential flow) filtration systems can often attain higher fluxes and higher throughputs than corresponding normal flow membrane filter systems. Suitable membranes include ultrafiltration, microporous, nanofiltration or reverse osmosis filters formed from polyvinylidene fluoride (PVDF), polysulfone, polyethersulfone, polyarylsulfone, regenerated cellulose, polyamide, polypropylene, polyethylene, polytetrafluoroethylene, cellulose acetate, polyacrylonitrile, vinyl copolymer, polyamides (such as "Nylon 6" or Nylon 66") polycarbonate, PFA, blends thereof or the like.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Additional aspects and advantages of the invention will be set forth in the description that follows, and in part will be obvious from the description, or may be learned by practice of the invention. Moreover, the aspects and advantages of the invention may be realized and obtained by means of the instrumentalities and combinations particularly pointed out in the appended claims.

BRIEF DESCRIPTION OF THE DRAWINGS

The accompanying drawings illustrate presently preferred embodiments of the present disclosure, and together with the general description given above and the detailed description given below, serve to explain the principles of the present disclosure. As shown throughout the drawings, like reference numerals designate like or corresponding parts.

FIG. 1 is a depiction of a Flowpath of a process flow of an exemplary embodiment of a Crossflow Filtration system for processing a biofluid incorporating aspects of the present disclosure.

DETAILED DESCRIPTION

The various diagrams, flow charts and scenarios described herein are only examples, and there are many other scenarios to which the present disclosure will apply.

Crossflow Filtration Systems generally comprise a series of tubes, valves, sensors, and conduits connected together to form a Flowpath. In these systems, an Internal Pump operably linked to a Sterile Air Source is located near the terminus of the Crossflow Filtration System adjacent to a Biofluid Source Container. In one particular embodiment, the Internal Pump operably linked to a Sterile Air Source is located at the terminus of the Crossflow Filtration System adjacent to a Biofluid Source Container.

i. As shown in the tangential Crossflow Filtration System 20 of FIG. 1, a collection of conduits 10 are provided (or otherwise present) to establish passageways and avenues for the circulation and/or flow of sample liquid to or among the various system components and sub-modules. While the number, pattern, and complexity of the conduits will vary depending on the number of system components and sub-modules, in a basic embodiment of the inventive system, the conduits 10 should at the least define, together with the Biofluid Container 1a, Recirculating Pump 2, Internal Pump 4, Sterile Air Source 5, Drain Valve 6, Valves 7, Pressure valves 8, Connections 9 and the Crossflow Filtration Filter 3, a fluid process stream through which the biofluid is conducted, the process stream flowing from said Biofluid Container 1a, into said Crossflow Filtration Filter 3, and back to said Biofluid Container 1a. The system may comprise a Feed Flow Line 11 operably linked from said Biofluid Container, e.g. via the Recirculating Pump, to said Crossflow Filtration Filter containing Feed Flow, a Retentate Flow Line Return 12 operably linked from said Crossflow Filtration Filter to said Biofluid Container; said Retentate Flow Line Return containing unFiltered Flow, and a Permeate Flow Line 13 operably linked to said Crossflow Filtration Filter containing (filtered) Permeate Flow. Further, the system may comprise a Drain Line 14 operably linked by a Drain Valve 6 to said Feed Flow Line.

There are no particular limitations to the type of conduit used. Potential conduit types include, for example, rigid pipes, flexible tubing, and the channels and passages formed in or intrinsic to the device. Other components include valves and connections). Typically, the plurality of conduits employed in the process development device will include a mixture of conduit types. In a preferred embodiment, the bulk of the conduits employed are flexible, substantially biologically inert, synthetic polymeric tubing having an internal diameter of approximately 0.100 inches (0.254 cm).

A plurality of valves 7 are positioned along or otherwise functionally proximate the fluid process stream for regulating the flow of liquid sample therethrough. In operation, flow of liquid through a valve will depend upon whether the valve is in an "open" or "closed" state or—in some circumstances—an intermediate state.

As indicated, a plurality of pumps 2 are positioned along or otherwise functionally proximate the device's fluid process stream to drive the flow of liquid sample therethrough. 1. It is understood that the system may have multiple configurations, for instance a pump on the permeate line. While pumps are preferred, other electronically-controllable means for driving sample liquid through the fluid process stream may be used.

In the automated CFF/TFF system illustrated in FIG. 1, in-line pumps are utilized including positive displacement pumps including peristaltic, transfer, diaphragm, centrifugal, high-pressure positive displacement (HPPD) and solenoid-activated diaphragm pumps. Although pumps are integrated into the system architecture they may thus still be modular so as to further facilitate single use operations where appropriate. Other pump configurations—e.g., piezoelectric-driven, acoustically-driven, thermopneumatically-driven, electrostatically-driven, etc.—may be employed. Potentially useful fluidic micropump devices are disclosed, and/or suggested, and/or mentioned in, for example, U.S. Pat. No. 5,338,164, issued to R. F. Sutton et al. on Aug. 16, 1994; U.S. Pat. No. 4,938,742, issued to J. G. Smits on Jul. 3, 1990; U.S. Pat. No. 6,283,718, issued to A. Prosperetti et al. on Sep. 4, 2001; and U.S. Pat. No. 5,759,015, issued to H. Van Lintel on Jun. 2, 1998, which are hereby incorporated by reference in their entireties.

The solenoid-actuated diaphragm pumps are self priming, micro-dispensing, solenoid actuated micropumps, capable of providing a non-metallic, inert fluid path for the dispensing of high purity or aggressive fluids. Such pumps are available from Bio-Chem Valve, Inc. of Boonton, N.J. 07005.

The high-pressure positive displacement (HPPD) pumps operate such that the driven flow of liquid sample does not fluctuate unacceptably together with back pressure. HPPD pumps include rotary reciprocating pumps such as disclosed in U.S. Pat. No. 5,863,187, issued to D. S. Bensley et al. on Jan. 26, 1999 (hereby incorporated by reference in its entirety), and available from Ivek Corporation of North Springfield, Vt. 05150. In the interest of reducing the device's minimum recirculation volume, the HPPD pumps should be configured to eliminate or otherwise reduce the so-called "dead spaces" where fluid can collect.

A reciprocating pump can suitably comprise a reciprocating moving member, such as e.g. a diaphragm, a membrane or a piston. A reciprocating moving member can move back and forth in relation to a pump chamber (also called a cylinder, when the moving member is a piston), forcing fluid (e.g. culture liquid) out from the pump chamber during an inward stroke of the moving member and sucking fluid (e.g. culture liquid) into the pump chamber during an outward stroke. The stroke volume of the reciprocating pump corresponds to the fluid (culture liquid) volume displaced out from or into the pump chamber during each stroke. The reciprocating pump may e.g. be a fluid-driven diaphragm pump, with a pump chamber and a drive fluid-filled drive chamber separated by a flexible diaphragm, which constitutes the reciprocating moving member. The drive fluid can be a gas, e.g. air, or a liquid. When fluid pressure is applied to the drive chamber via a drive fluid supply line, the diaphragm expels liquid from the pump chamber in an inward stroke and when the fluid pressure is released, the diaphragm flexes back and draws liquid into the pump chamber in an outward stroke. The pump chamber may e.g. be directly connected to the retentate inlet compartment of the filter unit. Alternatively, it may be connected via a fluid connector (not shown), such as a short piece of tubing with a diameter large enough not to impede the liquid flow and a volume significantly smaller than the stroke volume of the reciprocating pump (e.g. less than 20% of the stroke volume, such as less than 10% or less than 5% of the stroke volume), optionally via an aseptic connector.

Pumps, particularly the Internal Pump, when activated (e.g. turned on), induces a pressure in the Flowpath. Such pressure is amenable to various characterizations and methods of measure. Many such measures are framed in light of the manufacturing conditions used to create the pump. One such measure is rotations per minute (rpm) which refers to the rotation of a pressurizing mechanism around an axis or shaft, such as an impeller, in which the rpm describes the induced pressure. Other pressure measures may refer to flow output which measures the output of liquid per unit time expelled from a tube. Alternatively pressure may refer to psi (pounds per square inch) which is a unit of pressure or of stress based on avoirdupois units. The pressure describes the result from a force of one pound-force applied to an area of one square inch. Numerous methods are available to calculate or measure psi and may include so-called absolute, gauged or differential. Such descriptors are typically provided by each pump manufacturer.

In certain embodiments induction of an internalized pressurized Flow is activated by an Internal Pump pressuring flow between 10-10,000 rpm. Another embodiment refers to induction of an internalized pressurized flow by an Internal Pump pressuring flow between 100-1000 rpm.

An alternate embodiment refers to induction of an internalized pressurized flow output of from 1 mL/min to 1 L/min.

Another alternate embodiment refers to induction of an internalized pressurized flow between standard pressure (1 psi) to 150 psi.

Another alternate embodiment refers to induction of an internalized pressurized flow between 14 to 100 psi.

Another alternate embodiment refers to induction of an internalized pressurized flow between 14 to 50 psi.

Another embodiment refers to the control of displaced volume when using the pump.

By use of a pump, control of either displaced volume and/or the pressure downstream from the pump and upstream the filter and flow path to be evacuated from the liquid to be recovered can be secured. This promotes two advantages: a) the process is very gentle and minimizes foaming as it allows the system to be run at slower and at lower pressure. Further, b) accurate control of the amount of fluid (air) being displaced downstream the pump is important when the fluid is recovered in a sterile fashion by emptying it into a bag, for example. Knowledge of the displaced volume improves safety as the bag cannot inflate in an uncontrolled manner. monitor the pressure downstream the pump and upstream the fluid outlet for recovery to determine a pressure vs. time profile that can indicate that all fluid is replaced. This automation also allows for better process documentation (E-batch records of the GMP process), which eventually increases product and patient safety.

The Sterile Air source may also be supplied under pressure. In one embodiment it is supplied passively. In another embodiment it may be supplied at a rate from about 1 to 10 liters per minute.

Another method to measure the Sterile Air flow is in terms the amount of air that can be provided per unit time. According to such measure, another embodiment refers to pressuring air flow at about 2 liters per minute.

Another method to describe Air flow is measured in terms of a percentage of pump flow rate. According to such method, another embodiment refers to Air flow in the range of from 1 to 100% of Flowrate.

Another embodiment refers to pressurized flow at about 25% of maximum flow rate.

Crossflow Filtration Filters are well known in the literature. Such filters may include a cylindrical outer membrane surface symmetrically located about the axis and enclosing a filtrate chamber that is in fluid communication with the filtered fluid outlet. Although they are frequently shaped as a simple cylinder, other configurations may be used including stepped and conical shaped filters. The membrane surface may be fabricated from a wide variety of materials including porous polymers, ceramics and metals. In one embodiment, the membrane is relatively thin, e.g. from 0.2-0.4 mm and may be supported by an underlying rigid frame or porous support. One example is described in US2012/0010063. The pore size (e.g. 1 to 500 micron), shape (e.g. V-shape, cylindrical, slotted) and uniformity of the membrane surface may vary depending upon application. In many embodiments, the membrane surface comprises a corrosion-resistant metal (e.g. electroformed nickel screen) including uniform sized pores having sizes from 5 to 200 microns, or even 10 to 100 microns. Examples of such materials are described: U.S. Pat. Nos. 7,632,416, 7,896,169, US2011/0120959, US 2011/0220586 and US2012/0010063.

For certain biopharmaceutical applications in which the sample liquid under investigation has substantial and significant protein content, forces and circumstances that can lead to the unintended and undesired denaturation of said proteins (i.e., the loss of the physical conformation of the protein's polypeptide constituency) should be avoided and/or mitigated. The mechanical shear forces often produced in the operation of certain pumps, particularly at gas/liquid interfaces (e.g., bubbles), have been linked to protein denaturation, and accordingly, should be mitigated and/or avoided in the selection, manufacture, and incorporation of the device.

A plurality of sensors (not shown) may be positioned along or otherwise functionally proximate the fluid process stream, each sensor capable of acquiring data about the liquid sample in their respective areas of sensitivity. The types of data desirably acquired are those pertaining to the crossflow (also known as tangential flow) filtration process under investigation and relevant to the upward linear scaling thereof, and typically includes, but is not limited to, temperature, pH, pressure, concentration, flow rate, conductivity, flow rate and the like. Any detectors, probes, meters, and like sensing devices capable of acquiring such data can be utilized. Those skilled in the art will know of objectives for and methods of incorporating such sensing devices into the device. Incorporation will involve, among other things, establishment of connectivity with the data processing network 7.

"High-Performance Tangential Flow Filtration" (HPTFF), or HPCFF, refers to one embodiment that is often employed to produce up to 1000 fold purification factors of protein mixtures containing similarly sized species. This is normally not possible in traditional size-exclusion based membrane processes. HPTFF technology exploits differences in the size and thickness of the ionic cloud surrounding proteins. This thickness can be manipulated by changing the pH and ionic strength of a sample solution. Further details regarding HPTFF technology can be found, for example, in R. van Reis et al., Biotech, Bioeng., 56, 71-82, 1997; S. Saksena et al., Biotech. Bioeng., 43, 960-968, 1994; R van Reis et al., J. Membrane Sci., 129, 19-29, 1997; S. Nakao et al., Desalination, 70, 191-205, 1988; U.S. Pat. No. 5,256,294, issued to R. van Reis in 1993; and U.S. Pat. No. 5,490,937, issued to R. van Reis in 1996.

Example 1

A Crossflow Filtration System as described in FIG. 1 was constructed and activated with biofluid from a bioreactor. The cycling of the biofluid through the system results in concentration of the biofluid in the Biofluid container and the collection of waste from the permeate line. Pressurized flow from inline pump 2 is discontinued and countercurrent flow is initiated from an Internal Pump operably linked to said Retentate Flow Line Return and a Sterile Air Source. Valves to the biofluid container are sealed and a Drain line value is opened allowing the flow of concentrated biofluid to drain from the system and be recovered.

To avoid infection of the biofluid, all system components in contact with the biofluid should be suitable sterilized before cultivation. The system or parts of the system may be assembled and sterilized by autoclaving or radiation, or one or more components may be pre-sterilized and assembled in a sterile system. To facilitate assembly, the sterilized system parts or components may be equipped with aseptic connectors, e.g. of the ReadyMate type (GE Healthcare). Alternatively, the sterilized system parts/components may be contained in aseptic packages and assembled in a sterile clean room.

In yet another embodiment, the pressurizing method may also be used to a) recovery fluid at the permeate side of the filter. In this embodiment, a pump is connected to the top connection at the permeate side of the filter and the pressure would push fluid quantitatively through a CFF filter towards the end of the process to allow for quantitative processing.

Thus, while there have been shown, described and pointed out, fundamental novel features of the invention as applied to the exemplary embodiments thereof, it will be understood that various omissions and substitutions and changes in the form and details of devices and methods illustrated, and in their operation, may be made by those skilled in the art without departing from the spirit or scope of the invention. Moreover, it is expressly intended that all combinations of those elements and/or method steps, which perform substantially the same function in substantially the same way to achieve the same results, are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A process for enhanced recovery of a biological fluid from an activated crossflow filtration system, the process comprising:
   a. inducing an internalized pressurized countercurrent flow throughout the activated crossflow filtration system by activating an internal pump fluidically coupled to a sterile air source at a first end of the activated crossflow filtration system to cause said biological fluid to flow in a flow direction from the sterile air source toward a drain valve and opposite to a crossflow direction,
   b. recovering said biological fluid at the drain valve fluidically coupled at a second end opposite the first end of the activated crossflow filtration system,
      wherein the crossflow direction is along a fluid loop from a biofluid source container to a crossflow filtration filter and back to the biofluid source container,
      wherein the activating of the internal pump causes sterile air from the sterile air source to be introduced into the fluid loop between the biofluid source container and the crossflow filtration filter, and
      wherein said inducing of the internalized pressurized countercurrent flow comprises supplying sterile air from the sterile air source passively.

2. The process according to claim 1, wherein said internal pump is a peristaltic pump.

3. The process according to claim 1, wherein said activated crossflow filtration system comprises a series of tubes, valves, sensors, and conduits connected together to form a flowpath.

4. The process according to claim 1, wherein said internal pump is located adjacent to the biofluid source container.

5. The process according to claim 1, wherein activating said internal pump comprises operating said internal pump between 10-10,000 rpm.

6. The process according to claim 1, wherein activating said internal pump comprises operating said internal pump between 100-1000 rpm.

7. The process according to claim 1, wherein activating said internal pump comprises operating said internal pump to generate an air flow output of from 1 mL/min to 1 L/min.

8. The process according to claim 7, wherein said internal pump generates pressure between 1 psi to 150 psi.

9. The process according to claim 7, wherein said internal pump generates pressure between 14 to 100 psi.

10. The process according to claim 1, wherein said internal pump generates pressure between 14 to 50 psi.

11. The process according to claim 1 for enhanced recovery of a biological fluid from the activated crossflow filtration system wherein said internal pump induces air flow at about 2 L/min.

12. The process according to claim 1 for enhanced recovery of a biological fluid from the activated crossflow filtration system wherein said induction of the internalized pressurized countercurrent flow is about 25% of a maximum flow rate.

* * * * *